United States Patent
Pflueger

Patent Number: 6,013,038
Date of Patent: Jan. 11, 2000

[54] MAGNETIC GUIDEWIRE ANCHORING APPARATUS AND METHOD FOR FACILITATING EXCHANGE OF AN OVER-THE-WIRE CATHETER

[75] Inventor: Russell Pflueger, Laguna Niguel, Calif.

[73] Assignee: Advanced Cardiovascular Systems, Inc., Santa Clara, Calif.

[21] Appl. No.: 08/823,426

[22] Filed: Mar. 24, 1997

Related U.S. Application Data

[63] Continuation of application No. 08/370,932, Jan. 10, 1995, abandoned.

[51] Int. Cl.⁷ ....................................................... A61B 5/00
[52] U.S. Cl. ............................. 600/585; 604/96; 604/280
[58] Field of Search .............................. 600/585; 604/95, 604/96, 280, 281, 282

[56] References Cited

U.S. PATENT DOCUMENTS

| | | | |
|---|---|---|---|
| 3,674,014 | 7/1972 | Tillander | 128/657 |
| 4,728,319 | 3/1988 | Masch | 604/22 |
| 4,809,713 | 3/1989 | Grayzel | 607/116 |
| 5,255,690 | 10/1993 | Keith et al. | 128/772 |
| 5,269,759 | 12/1993 | Hernandez et al. | 604/96 |
| 5,357,978 | 10/1994 | Turk | 128/772 |
| 5,464,023 | 11/1995 | Viera | 128/772 |
| 5,487,729 | 1/1996 | Avellanet et al. | 604/96 |
| 5,606,980 | 3/1997 | Calhoun et al. | 600/585 |

FOREIGN PATENT DOCUMENTS

| | | |
|---|---|---|
| 0 440 345 | 8/1991 | European Pat. Off. . |
| 1283453 | 8/1970 | United Kingdom . |

Primary Examiner—Cary O'Connor
Assistant Examiner—Pamela L. Wingood
Attorney, Agent, or Firm—Heller, Ehrman, White & McAuliffe

[57] ABSTRACT

A magnetic guidewire anchoring apparatus for deterring longitudinal movement of a guidewire during manipulation or exchange of an over-the-wire catheter. The magnetic guidewire anchoring apparatus may comprise permanent magnet(s) or electromagnet(s), and may incorporate configuration attributes and/or attendent mounting brackets or other apparatus to facilitate positioning of the apparatus on the outer surface of a catheter through which a guidewire extends.

14 Claims, 3 Drawing Sheets

ND METHOD FOR
FACILITATING EXCHANGE OF AN OVER-
THE-WIRE CATHETER

This is a continuation of application Ser. No. 08/370,932 which was filed on Jan. 10, 1995, now abandoned.

FIELD OF THE INVENTION

The present invention pertains generally to medical equipment and, more particularly, to a magnetic apparatus for supporting a guidewire during exchange of an over-the-wire catheter.

BACKGROUND OF THE INVENTION

Percutaneous Transluminal Angioplasty Procedures are commonly utilized in clinical practice as methods for treating vascular obstructions. In particular, coronary angioplasty procedures have become widely utilized for restoring patency to obstructed or partially obstructed coronary arteries.

At present, two general types of balloon angioplasty catheters are utilized in clinical practice—The "full length over-the-wire" catheter and the "monorail" catheter.

i. Monorail Catheters

In a "monorail" style of angioplasty catheter, a guidewire lumen extends through only a distal portion of the catheter, typically from a distal tip aperture to a proximal aperture formed in the side wall of the catheter body. Accordingly, as the catheter is advanced over the prepositioned guidewire, the proximal end of the guidewire will emerge from the side wall aperture such that the proximal portion of the guidewire remains outside of the catheter body as the catheter is advanced to its desired operative site. If it becomes necessary or desirable to exchange the balloon dilation catheter, the proximally exposed portion of the guidewire can be manually held and stabilized by the operator while the first catheter is removed and a second catheter is slid over the pre-positioned guidewire. Since the length of the catheter that must be passed over the guidewire is lessened in the "monorail" type of arrangement, it is typically easier for the operator to manually stabilize the guidewire during the exchange procedure and the need for a proximal extension or excessively long guidewire is eliminated.

ii. Over-the-Wire Catheters

The "over-the-wire" style of angioplasty catheter incorporates, a guidewire lumen which extends substantially through the entire length of the catheter. The guidewire lumen is separate from the balloon inflation lumen.

iii. Typical Methods for Catheter Exchange During Percutaneous Transluminal Angioplasty Procedures In a typical balloon angioplasty procedure, a guidewire is percutaneously inserted and advanced through the vasculature to a point where the distal end of the guidewire is adjacent, or has passed through, the stenotic lesion or other obstruction to be treated. Thereafter, the balloon dilation catheter is advanced over the prepositioned guidewire until the balloon is across the stenotic lesion or obstruction. Subsequent inflation of the balloon then effects dilation of the stenotic lesion or obstruction. If, during the angioplasty procedure, it becomes necessary or desirable to remove the full length over-the-wire catheter and replace it with another full length over-the-wire catheter, it is typically necessary to attach an extension on the proximal end of the guidewire (or to use an excessively long guidewire) so that a sufficient length of guidewire extends outside of the body to allow the operator to maintain an manual grasp and stabilization of the guidewire while one catheter is removed and the other catheter is subsequently inserted. Inadvertent longitudinal retraction of the guidewire during the catheter exchange procedure is undesirable because subsequent re-advancement of the guidewire through the stenotic lesion may be complicated due to breakage or collapse of the obstructive matter and/or the occurrence of vasospasm.

Because the exchange of an over-the-wire catheter requires the use of an excessively long guidewire, or a proximal guide extension, and in view of the attendant cumbersomeness of effecting such exchange of an over-the-wire type of catheter, there exists a need in the art for improved methods and apparatus for stabilizing and holding a prepositioned guidewire during the exchange of an over-the-wire type of catheter.

SUMMARY OF THE INVENTION

The present invention provides a magnetic guidewire stabilizing apparatus for preventing or minimizing longitudinal movement of a prepositioned cardiovascular guidewire. The magnetic guidewire stabilizing apparatus of the present invention is useable to prevent inadvertent retraction of the guidewire while exchanging on over the wire catheter for another.

In accordance with the invention, the magnetic guidewire stabilizing apparatus may comprise an apparatus which is separately positionable on, or close to a catheter or guidewire. Alternatively the magnetic apparatus may be integrated into the body and/or proximal connector of a catheter to facilitate magnetic holding of a guidewire which passes through the catheter.

Further in accordance with the invention there is provided a method for exchanging an over-the-wire type of catheter by applying a magnetic field to prevent or deter longitudinal movement of the guidewire during the catheter exchange procedure.

BRIEF DESCRIPTION OF THE DRAWINGS

FIG. 4b is an enlarged view of a portion of FIG. 4a.

DETAILED DESCRIPTION OF THE PREFERRED EMBODIMENTS

The following detailed description in the accompanying drawings are provided for purposes of describing and illustrating presently preferred embodiments of the invention only, and are not intended to limit the scope of the invention in any way.

Figure 1:
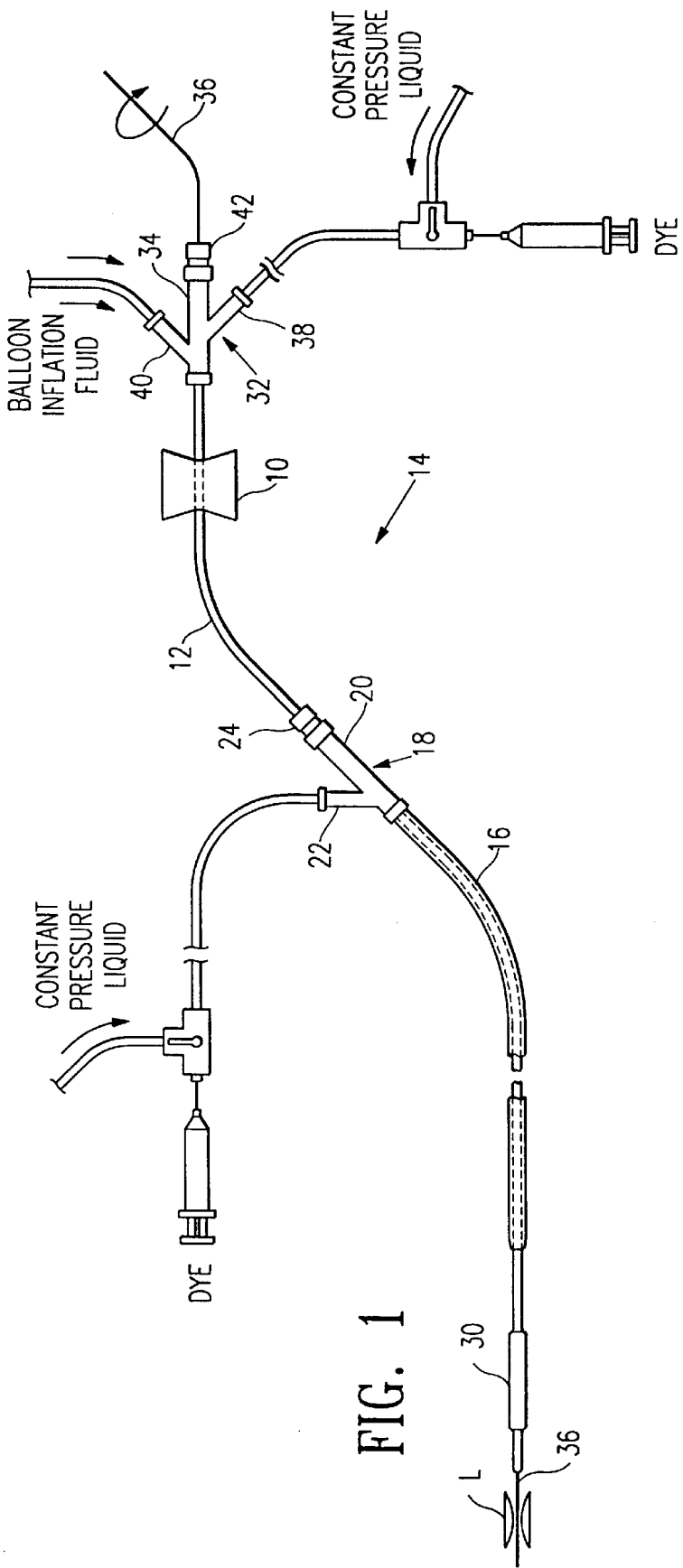
FIG. 1 is a schematic diagram of a typical balloon angioplasty system having a magnetic guidewire anchoring apparatus of the present invention operatively positioned thereon.

FIG. 1 shows a magnetic guidewire holding apparatus 10 of the present invention operatively positioned on an over-the-wire balloon angioplasty catheter 12. The catheter 12 is shown in conjunction with a typical balloon angioplasty system 14.

As shown, the overall balloon angioplasty system 14 comprises a tubular guiding catheter 16 having a Y-adaptor 18 formed on the proximal end thereof. The Y-adaptor 18 includes a first furcation 20 through which the balloon catheter 12 is passed and a second furcation 22 through which fluids (e.g., radiographic contrast medium, saline flush) may be infused through the lumen of the guide catheter 16. A valving/gripping apparatus 24 is provided on the proximal end of the first furcation 20. Such valving/gripping apparatus 24 may be tightened about the outer surface of the balloon catheter 12 to hold the balloon catheter 12 in a fixed position following insertion thereof. Such valving apparatus 24 may be of the type commercially available as product nos. 1905017A and/or 190501A from Medical Disposables International, West Conshocken, Pa.

The balloon catheter 12 comprises an elongate catheter body having a dilation balloon 30 formed near the distal end thereof. A trifurcated adaptor 32 is formed on the proximal end of the balloon catheter 12. Such trifurcated adaptor 32 comprises a first furcation 34 through which a guidewire 36 may be passed, a second furcation 38 through which fluid (e.g., radiographic contrast medium, saline flush) may be infused and a third furcation 40 through which balloon inflation fluid may be infused. A second valving/gripping apparatus 42 is provided on the first furcation. Such second valving/gripping apparatus may also be of the type commercially available as product nos. 1905017A and/or 190501A from Medical Disposables International, West Conshocken, Pa. Such valving apparatus 42 may be tightened about the outer surface of the guidewire 36 to hold the guidewire in a fixed position relative to the balloon catheter 12.

Figure 4A:
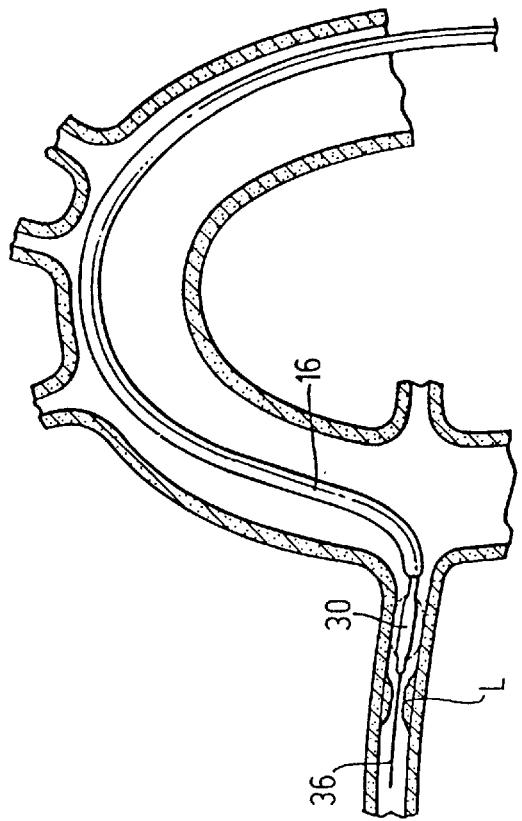
FIG. 4a is a diagram of a human aortic arch, showing a balloon angioplasty catheter system, including a guidewire, positioned within a coronary artery.
Figure 4B:
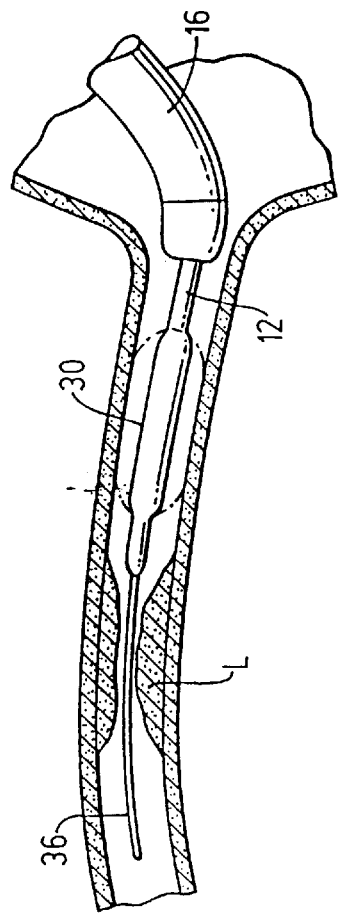
Figure 3:
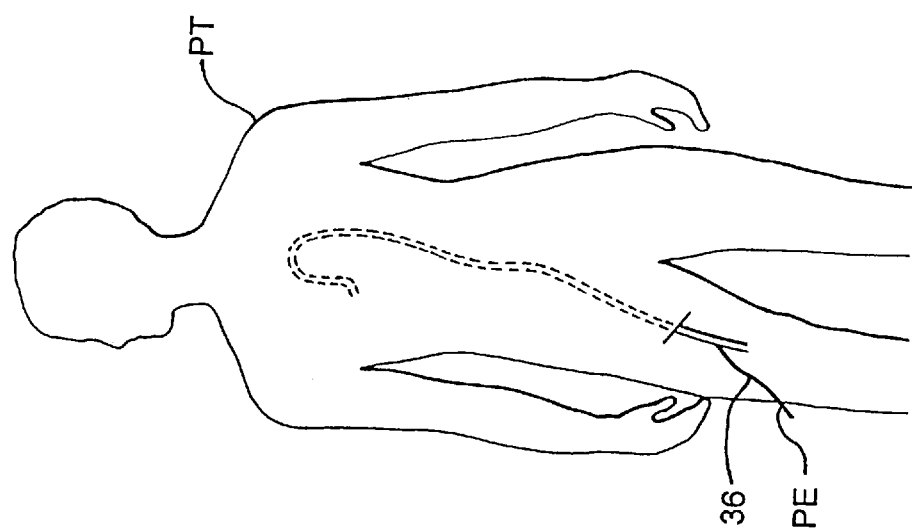
FIG. 3 is a diagram of a human body showing a typical percutaneous coronary artery catheterization route.

The typical balloon catheter system 14 shown in FIGS. 4a and 4b may be utilized in accordance with standard clinical protocols for balloon angioplasty. In accordance with one such typical protocol, the guidewire 36 may be initially inserted into the vasculature, through a percutaneous introducer positioned within the femoral artery or other peripheral artery. Thereafter, as shown in FIGS. 3–4b, the guidewire 36 may be advanced through the aorta to a point where the distal end of the guidewire is positioned near the coronary ostia. Thereafter, the proximal end PE of the guidewire 36 may be inserted into the distal end of the guide catheter 16, and the guide catheter 16 may be advanced over the previously inserted guidewire 36. The guide catheter 16 is maneuvered into its desired position whereat the distal end of the guide catheter 16 is positioned within or adjacent the desired coronary ostium. Thereafter, the guidewire 36 may be further advanced through the lesion L to be treated. Thereafter, the proximal end PE of the guidewire 36 may be inserted into the distal end of the balloon catheter 12, and the balloon catheter 12 may then be advanced over the guidewire 36 to a point where the distal end of the balloon catheter 12 is adjacent the lesion L to be treated. The balloon catheter 12 is then carefully advanced to a position where the balloon 30 extends across the lesion L and the balloon 30 is inflated by passing balloon inflation fluid through the third furcation 40 of the balloon catheter 12 so as to inflate the dilation balloon 30, thereby dilating the lesion L. Thereafter, the guidewire 36, balloon catheter 12 and guiding catheter 16 may be retracted and removed from the patient PT. If, during the performance of the balloon angioplasty procedure, it is desired to anchor the balloon catheter 12 in a desired position relative to the guiding catheter 16, such may be done by tightening the valving apparatus 24 on the proximal end of the guiding catheter 16. Similarly, if it is desired to anchor the balloon catheter 12 relative to the guidewire 36, such may be accomplished by tightening the valving apparatus 42 on the proximal end of the balloon catheter 12.

Sometimes, during the performance of endovascular catheter-mediated procedures, such as the above-described balloon angioplasty procedure, it may be desirable to effect a "catheter exchange" whereby one of the catheters is removed and replaced with a different catheter prior to completion of the procedure. The need to perform such "catheter exchange" may arise in balloon angioplasty procedures if the balloon catheter 12 is not sized or configured such that the balloon 30 may be easily passed across the lesion L.

Effecting catheter exchange during an endovascular procedure may be complicated by the fact that it may be undesirable to move the guidewire 36 after it has been properly positioned within the lesion L or elsewhere. Recognizing this concern, others have attempted to devise methods for holding the guidewire 36 in place while a catheter, such as the balloon catheter 12, is removed and replaced. Prior art devices which have been utilized to facilitate such exchange of a balloon catheter 12 include a guidewire extension which may be coupled to the proximal PE of the guidewire 36 to provide an extension which is longer than the overall length of the balloon catheter 12 to be removed. By such arrangement, the operator may continually stabilize the guidewire 36 by grasping an exposed portion of the attached guidewire extension while the balloon catheter 12 is proximally retracted. After the distal end of the balloon catheter 12 has emerged from the proximal Y-adaptor 18 of the guiding catheter 16, the operator may then grasp an exposed portion of the guidewire 36 between the distal end of the balloon catheter 12 and the proximal end of the proximal Y-adaptor 18 of the guide catheter 16. Thereafter, first balloon catheter 12 may be proximally retracted off of the guidewire 36 and guidewire extension. Thereafter, a replacement guide catheter must be advanced over the guidewire 36 and guidewire extension, with the operator endeavoring to maintain a manual grasp of the guidewire 36 and/or guidewire extension so as to prevent inadvertent longitudinal movement of the guidewire 36.

The magnetic guidewire anchoring apparatus 10 of the present invention eliminates the need for a guidewire extension, or for manual grasping of the guidewire 36 while exchanging the balloon catheter 12. In this regard, the magnetic guidewire anchoring apparatus 10 is positioned adjacent the outer surface of the balloon catheter 12 or guide catheter 16 such that the magnet field created by the magnetic apparatus 10 will engage the guidewire 36 within the catheter 12 or 16 so as to effectively hold the guidewire 36 in a substantially fixed longitudinal position while the catheter 12 or 16 is retracted, and a replacement catheter is advanced over the guidewire 36.

It will be appreciated that the magnetic guidewire anchoring apparatus 10 of the present invention may be configured and constructed in various different ways, utilizing either permanent magnet(s) or electromagnet(s) or combinations thereof.

Figure 2:
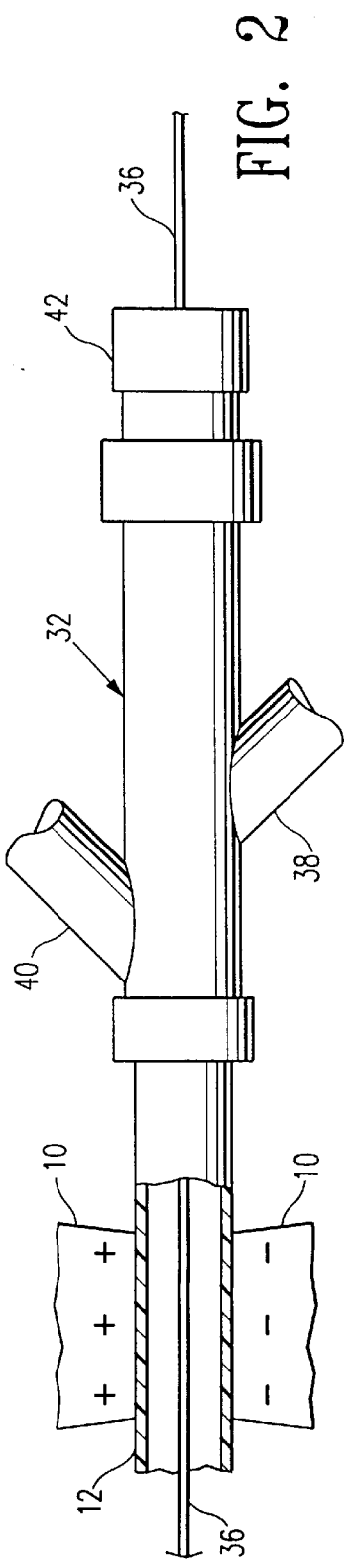
FIG. 2 is an enlarged view of a portion of the balloon angioplasty catheter shown in FIG. 1, including a magnetic guidewire anchoring apparatus of the present invention positioned thereon.
Figure 5:
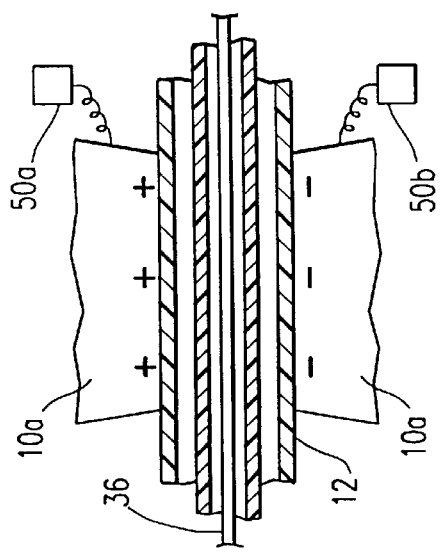
FIG. 5 is a schematic showing of an alternative electromagnetic apparatus of the present invention.
Figure 6:
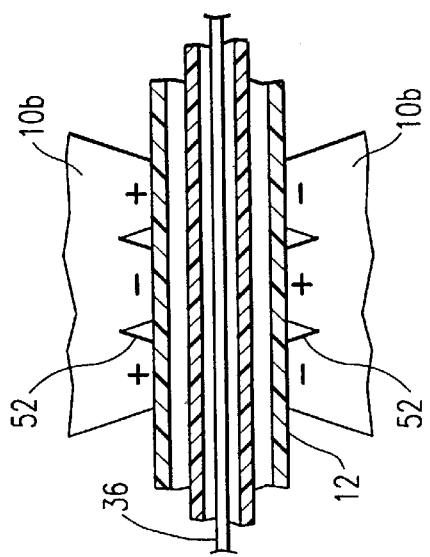
FIG. 6 is a schematic showing of an alternative alternating pole magnetic apparatus of the present invention.
Figure 7:
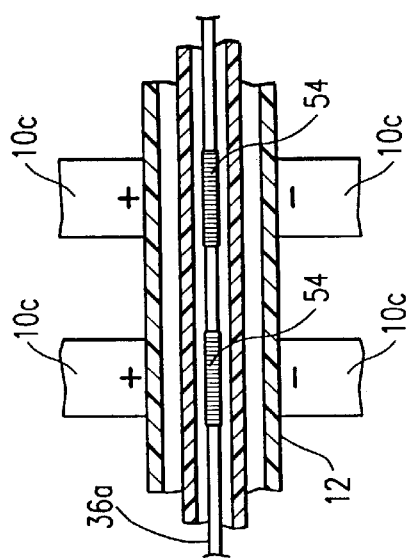
FIG. 7 is a schematic showing of an alternative multiple magnet guidewire anchoring apparatus of the present invention.
Figure 8:
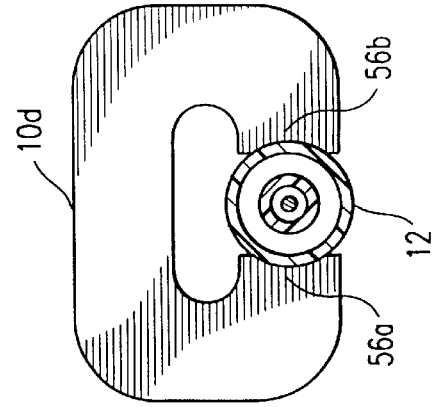
FIG. 8 is an elevational view of a "C" shaped magnetic guidewire anchoring apparatus of the present invention operatively positioned on a catheter having a guidewire extending therethrough.
Figure 9:
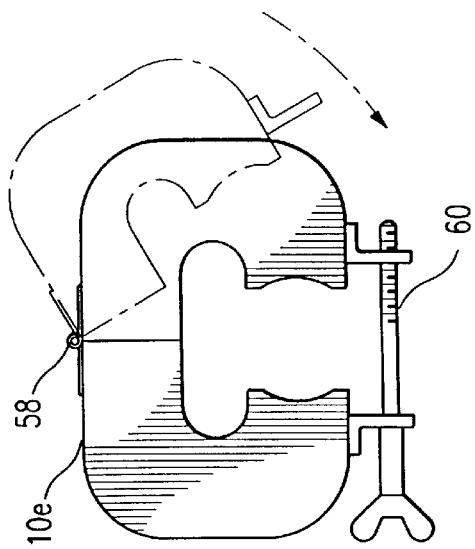
FIG. 9 is an elevational view of an alternative hinged magnetic guidewire anchoring apparatus of the present invention.

The basic embodiment of the magnetic guidewire anchoring apparatus 10 shown in FIG. 2 is depicted as a simple permanent magnet having positive poles positioned on one side of the catheter 12 and negative poles positioned on the opposite side of the side of the catheter 12. Alternative embodiments may incorporate pluralities of individual magnets, alternating magnetic polarities, and/or electromagnets as shown in FIGS. 5–7 and described herebelow. Also, the apparatus 10 may be constructed, configured, and equipped to facilitate clipping, clamping, snap-fitting, bracketing, or holding of the apparatus 10 on a catheter, as shown in FIGS. 8–9 and described herebelow.

In any embodiment of the invention, it will be appreciated that the magnetic guidewire anchoring apparatus may be in the form of a single magnet which is configured so as to bend or wrap around the catheter 12, thereby enabling opposite poles of the magnet to be positioned on opposite side of the catheter 12 as shown in FIG. 2. Alternatively, the magnetic apparatus 10 may be formed of separate magnets (e.g., bar magnets) positioned on opposite sides of the catheter 12 such that opposite poles of the separate magnets are aligned in the manner shown in FIG. 2.

FIG. 5 shows an alternative embodiment of the magnetic guidewire anchoring apparatus 10a wherein the apparatus is made up of one or more electromagnets. Such electromagnet(s) are connected to one or more power source(s) 50a, 50b. Such power source(s) 50a 50b may be volitionally actuated and deactuated by the operator to cause the magnetic field created by the apparatus 10a to turn on and off as needed.

FIG. 6 shows another alternative embodiment of the magnetic guidewire anchoring apparatus 10b wherein the magnet or magnets positioned on opposite sides of the catheter 12 have alternating regions of differing polarity. V-shaped notches 52 are formed in the opposing surfaces of the magnet(s) 10b, separating the regions of alternating polarity thereon. The magnet(s) 10b is/are positioned adjacent the outer surface of the catheter 12 such that opposite magnetic poles are aligned directly across from one another, thereby creating discrete lines of magnetic flux or magnetic fields running in opposite directions through the body of the catheter 12 and acting upon the guidewire 36.

FIG. 7 shows another alternative embodiment of a magnetic guidewire anchoring apparatus 10c wherein multiple individual magnets are arranged at spaced-apart locations on opposite sides of the outer surface of the catheter 12, thereby creating separate magnetic flux lines or magnetic fields which extend through the catheter 12 and act upon the guidewire 36.

Also shown in FIG. 7, in accordance with the present invention, the guidewire 36a may be provided with localized regions or segments 54 having greater ferromagnetic properties than the remainder of the guidewire 36a. For example, if the guidewire 36a is formed of nonferromagnetic material, a ferromagnetic metal core or metal foil wrapping may be disposed on the guidewire 36a in the localized regions or segments 54 wherein the ferromagnetic activity is to be present. By such arrangement, the magnetic guidewire anchoring apparatus 10c will act only upon the localized regions or segments 54 of the guidewire 36a having the ferromagnetic material disposed therein or thereon. Similarly, in embodiments wherein the guidewire 36a is formed of ferromagnetic material, the localized regions or segments 54 may contain additional or excess ferromagnetic material, or may be formed of excess mass or density relative to the remainder of the guidewire 36a, thereby enhancing the ferromagnetic properties of the guidewire 36a within the localized regions or segments 54 thereof. By such arrangement, the magnetic guidewire anchoring apparatus 10c will have enhances guidewire stabilizing effects when aligned with and acting upon the localized segments or regions 54 of enhanced ferromagnetic properties.

FIG. 8 shows an example of a magnetic guidewire anchoring apparatus 10d of the present invention having a "C" shaped configuration such that the opposite ends 56a 56b of the magnetic apparatus 10d may be positioned on opposite sides of the catheter 12. Also, in the embodiment shown, the opposite ends 56a, 56b of the magnetic apparatus 10d have radial depressions or cut-out regions formed therein, and are specifically spaced apart such that a catheter 12 of known diameter may be snap-fit into the opposing radial depressions or cut-out regions formed on the opposite surfaces of the C-shaped magnetic apparatus 10d. The manner in which the catheter 12 may be snap fit into the magnetic guidewire anchoring apparatus 10d is specifically shown in FIG. 8.

Figure 8A:
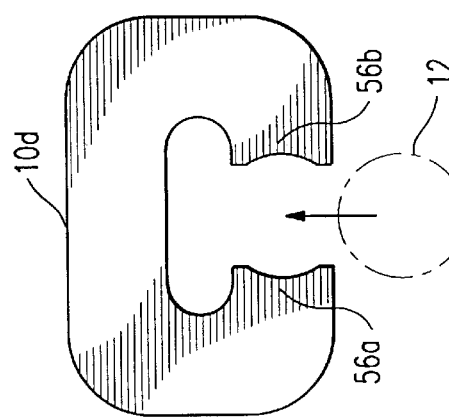
FIG. 8a is an elevational view of the "C" shaped magnetic guidewire anchoring apparatus of FIG. 8, with the catheter removed therefrom.

FIG. 9 shows another alternative embodiment of a magnetic guidewire anchoring apparatus 10e of the present invention, wherein the apparatus 10e has a "C" shaped configuration similar to that shown in FIGS. 8–8a, but wherein the apparatus 10e is transacted directly opposite the space wherein the catheter (not shown) is positioned and a hinge or bending member 58 is positioned on the body of the apparatus 10e so as to permit one or both of the opposing portions of the apparatus 10e to be bendably or pivotally moved, as shown. In this manner, the apparatus 10e may be pivotally or bendably closed about the outer surface of a catheter, irrespective of the outer diameter of the catheter. Also, as shown in FIG. 9, the apparatus 10 of the present invention may further incorporate a closure apparatus 60, such as a wing nut capable of securely tightening and holding the apparatus 10e about the outer surface of the catheter (not shown).

Although the magnetic guidewire anchoring apparatus 10 of the present invention has been described herein with reference to certain specific embodiments of the invention, it will be appreciated that various modifications, changes, deletions and alterations may be made to the herein described embodiments without departing from the intended spirit and scope of the invention. It is intended that all such foreseeable modifications, deletions, additions and alterations be included within the scope of the following claims.

What is claimed is:

1. A method for deterring longitudinal movement of a guidewire during exchange of a first catheter through which said guidewire extends with a second catheter, comprising:

a) providing a guidewire having at least one ferromagnetic region thereon, wherein said ferromagnetic region has a substantially uniform diameter;

b) positioning a magnet which has opposed poles defining an opening configured to radially receive the guidewire which is within the first catheter so that the opposed poles are on opposite sides of the guidewire, which produces a magnetic field substantially transverse to said guidewire such that said magnetic field will act on a ferromagnetic portion of said guidewire to magnetically deter longitudinal movement of said guidewire;

c) withdrawing and removing the first catheter; and d) passing a second catheter over said guidewire.

2. The method of claim 1 wherein at least one ferromagnetic region of the guidewire enhances the magnitude of magnetic attraction between said magnet and said guidewire.

3. The method of claim 2 wherein the ferromagnetic region of said guidewire comprises excess ferromagnetic material relative to the remainder of the guidewire.

4. The method of claim 2 wherein the ferromagnetic region of said guidewire comprises excess ferromagnetic density relative to the remainder of the guidewire.

5. A magnetic apparatus for deterring longitudinal movement of a guidewire formed at least partially of ferromagnetic material, during exchange of a catheter through which said guidewire extends, said apparatus comprising:

a magnet which has opposed poles defining an opening configured to radially receive the catheter and configured so that the opposed poles are on opposite sides of the catheter and guidewire so as to exert a magnetic field substantially transverse to the guidewire through said catheter to act on said guidewire to deter longitudinal movement thereof; and a housing attached to the magnet and configured to allow said catheter and guidewire to be positioned between said opposed poles.

6. A magnetic system for deterring longitudinal movement of a guidewire during exchange of a catheter, said system comprising:

a magnet which has opposed poles defining an opening configured to radially receive the catheter so that the opposed poles are on opposite sides of the guidewire which is disposed within said catheter so as to exert a magnet field substantially transverse to the guidewire through said catheter to act on said guidewire to deter longitudinal movement thereof ; and a region of enhanced ferromagnetic properties formed on said guidewire to enhance the magnitude of magnetic attraction between said magnet and said guidewire.

7. The system of claim 6 wherein said region of enhanced ferromagnetic properties comprises at least one region wherein the ferromagnetic mass of said guidewire, per unit of length, is greater than the ferromagnetic mass per unit of length covering the remainder of said guidewire.

8. The system of claim 6 wherein said region of enhanced ferromagnetic properties comprises at least one region wherein the ferromagnetic density of said guidewire, per unit of length, is greater than the ferromagnetic density per unit of length covering the remainder of said guidewire.

9. A magnetic system for deterring longitudinal movement of a ferromagnetic guidewire during exchange of an over-the-wire cardiovascular catheter through which said guidewire extends, said system comprising:

a magnet within a C-shaped housing positionable adjacent at least a portion of the catheter so as to exert a substantially transverse magnetic field through said catheter and guidewire to act on said guidewire to deter longitudinal movement thereof; and a region of enhanced ferromagnetic properties formed on said guidewire wherein the ferromagnetic density of the guidewire at said region, per unit of length, is greater than the ferromagnetic density per unit of length covering the remainder of the guidewire, wherein said region has a substantially uniform diameter.

10. A magnetic system for deterring longitudinal movement of a ferromagnetic guidewire during exchange of an over-the-wire cardiovascular catheter, said system comprising:

a C-shaped magnet within a C-shaped housing positionable adjacent at least a portion of the catheter wherein opposite poles of the magnet are positioned opposite one another separated by the catheter so as to exert a magnet field through said catheter to act on said guidewire to deter longitudinal movement thereof and;

a region of enhanced ferromagnetic properties formed on said guidewire to enhance the magnitude of magnetic attraction between said magnet and said guidewire.

11. The method for deterring longitudinal movement of a guidewire of claim 1 wherein the magnet is a C-shaped magnet having opposite ends which form the opposed poles which define the opening configured to radially receive the guidewire within the first catheter.

12. The magnetic apparatus of claim 5 wherein the magnet is a C-shaped magnet having opposite ends which form the opposed poles.

13. The magnetic system of claim 6 wherein the magnet is a C-shaped magnet having opposite ends which form the opposed poles.

14. The magnetic system of claim 9 wherein the magnet is a C-shaped magnet having opposite ends which form opposed magnetic poles which are positionable adjacent at least a portion of the catheter.

* * * * *